United States Patent [19]  [11] 4,088,696
Schreiber et al.  [45] May 9, 1978

[54] PROCESSES FOR PRODUCING ALKENALS AND INTERMEDIATES THEREFOR

[75] Inventors: William L. Schreiber, Jackson; Alan O. Pittet, Atlantic Highlands, both of N.J.

[73] Assignee: International Flavors & Fragrances Inc., New York, N.Y.

[21] Appl. No.: 788,355

[22] Filed: Apr. 18, 1977

Related U.S. Application Data

[62] Division of Ser. No. 664,830, Mar. 8, 1976, abandoned, which is a division of Ser. No. 383,579, Jul. 30, 1973, Pat. No. 3,922,309.

[51] Int. Cl.² ............................................. C07C 47/20
[52] U.S. Cl. ................................................. 260/601 R
[58] Field of Search ...................................... 260/601 R

[56] References Cited

U.S. PATENT DOCUMENTS

| | | | |
|---|---|---|---|
| 2,855,441 | 10/1958 | Sondheimer | 260/615 R |
| 3,078,256 | 2/1963 | Wittig et al. | 260/666 R |
| 3,920,701 | 7/1976 | Sanderson et al. | 260/601 R |
| 3,922,309 | 11/1975 | Schreiber et al. | 260/601 R |
| 4,024,190 | 5/1977 | Sanderson et al. | 260/601 R |

FOREIGN PATENT DOCUMENTS

| 1,793,713 | 2/1973 | Germany | 260/601 R |
|---|---|---|---|

Primary Examiner—James O. Thomas, Jr.
Assistant Examiner—Werren B. Lone
Attorney, Agent, or Firm—Arthur L. Liberman; Harold Haidt; Franklin D. Wolffe

[57] ABSTRACT

Processes for producing novel 2-alkylidene-3-alkynals and 2-alkylidene-3-alkenals which comprise reacting an alkyl metallo acetylide with a dialkoxy acetonitrile or a dialkoxy dialkyl acetamide to form an imine salt, hydrolyzing the imine salt to form a 1,1-dialkoxy-3-alkyn-2-one, alternatively (a) first treating the alkynone with an alkylidene tri-substituted phosphorane or an alkylidene phosphorous triamide or an alkyl phosphoramide anionic compound to provide a dialkoxy alkylidene alkyne, and then either (1) hydrolyzing the dialkoxy alkylidene alkyne to form a novel aldehyde, an alkylidene alkynal, and if desired, reducing the triple bond of the alkylidene alkynal to a double bond to obtain the corresponding alkylidene alkenal or (2) first reducing the dialkoxy alkylidene alkyne to form a 1,1-dialkoxy-2-alkylidene-3-alkene and if desired then hydrolyzing said 1,1-dialkoxy-2-alkylidene-3-alkene to form the desired 2-alkylidene-3-alkenal; or (b) first reducing the alkynone to form a 1,1-dialkoxy-3-alken-2-one and then treating the 1,1-dialkoxy-3-alken-2-one with an alkylidene tri-substituted phosphorane or an alkylidene phosphorous triamide or an alkyl phosphoramide anionic compound to provide a dialkoxy alkylidene alkene and, if desired, then hydrolyzing said dialkoxy alkylidene alkene to form the desired 2-alkylidene-3-alkenal; together with novel alkylidene alkynals and acetals thereof so produced.

1 Claim, No Drawings

PROCESSES FOR PRODUCING ALKENALS AND INTERMEDIATES THEREFOR

This application is a divisional of U.S. Application for Letters Patent Ser. No. 664,830 filed on Mar. 8, 1976, (now abandoned, which, in turn, is a divisional application of U.S. Application for Letters Patent Ser. No. 383,579 filed July 30, 1973 (now U.S. Pat. No. 3,922,309 issued on Nov. 25, 1975).

BACKGROUND OF THE INVENTION

The present invention relates to novel processes for producing 2-alkylidene-3-alkynals and 2-alkylidene-3-alkenals and to the novel alkynals, alkenals and acetals thereof so obtained.

U.S. Pat. No. 3,463,818 shows unsaturated aldehydes having various floral odors and processes for preparing such compounds. Japanese published application 72/43526 shows the synthesis of terpene derivatives having orange-like odors, and hexadienal derivatives are shown. Wiemann et al, *Memoires Presentes Soc. Chem.*, 1966, 1760, describe nuclear magnetic resonance studies of some conjugated dienals, and a number of these compounds, including 2-ethylidene-3-pentenal are shown. 2-Propenyl-2-pentenal is mentioned in *Chem. Abstracts* 35, 6238.

West German published application No. 1,951,883 is said in Chem. Abstracts 75, 5246 to show preparation of dienals useful as perfumes. Tiffeneau et al, *Comptes Rend.* 204, 590 show the preparation of 2-alkylidene-3-alkenals.

U.S. Pat. Nos. 3,272,873; 3,453,317; and 3,493,619 show processes for preparing unsaturated aldehydes or for treating such aldehydes. U.S. Pat. No. 3,520,936 shows production of an unsaturated aldehyde, and U.S. Pat. No. 3,542,878 shows an aldol condensation using a tin catalyst.

Odiger et al Annalen 682, 58 (1955); Corey et al, J. Am. Chem. Soc. 90, 6816; and Wittig et al, *Chem. Ber.* 94, 676 show "alkylidenation" reactions utilizing phosphorous compounds.

THE INVENTION

The processes of the present invention provide a relatively straightforward and convenient synthesis for obtaining 2-alkylidene-3-alkynals, acetals thereof and 2-alkylidene-3-alkenals and acetals thereof in good yields. Briefly, the processes comprise reacting an alkyl metallo acetylide with a dialkoxy acetonitrile or dialkoxy dialkyl acetamide and hydrolyzing the imine salt so obtained to form the corresponding 1,1-dialkoxy-3-alkyne-2-one, then, in the alternative either (a) treating the dialkoxy alkynone with an alkylidene triaryl substituted phosphorane, or an alkylidene phosphorous triamide or an alkyl phosphoramide anionic compound to form a 1,1-dialkoxy-2-alkylidene-3-alkyne and either (1) hydrolyzing the 1,1-dialkoxy-2-alkylidene-3-alkyne with aqueous acid to provide a 2-alkylidene-3-alkynal or (2) reducing the triple bond of the 1,1-dialkoxy-2-alkylidene-3-alkyne thus forming a 1,1-dialkoxy-2-alkylidene-3-alkene; or (b) first reducing (as by hydrogenation) the dialkoxy alkynone to form a 1,1-dialkoxy-3-alken-2-one and then treating the 1,1-dialkoxy-3-alken-2-one with an alkylidene triaryl substituted phosphorane, or an alkylidene phosphorous triamide or an alkyl phosphoramide anionic compound to form a 1,1-dialkoxy-2-alkylidene-3-alkene. The alkynals so obtained are novel compounds having the formula:

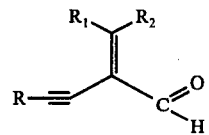

wherein one of $R_1$ and $R_2$ is hydrogen and the other is lower alkyl and R is lower alkyl. Such novel alkynals have a number of uses, one of which is hydrogenation of the triple bond to a double bond for production of the corresponding 2-alkylidene-3-alkenal compounds.

The 1,1-dialkoxy-2-alkylidene-3-alkenes so obtained are novel compounds having the formula:

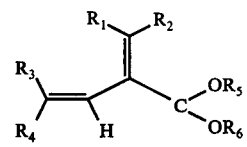

wherein one of $R_1$ and $R_2$ is hydrogen and the other is lower alkyl; wherein one of $R_3$ and $R_4$ is hydrogen and the other is lower alkyl; and wherein $R_5$ and $R_6$ are each the same or different lower alkyl (e.g. methyl, ethyl, n-propyl, isopropyl, isobutyl and n-butyl). These 2-alkylidene alkenal acetals can either be hydrolyzed to the corresponding 2-alkylidene-3-alkenal compounds or they can be used as precursors for such 2-alkylidene-3-alkenal compounds in flavor and/or aroma or fragrance imparting compositions (which are, in turn, used in conjunction with such consumable materials as perfumes, tobaccos, foodstuffs and beverages).

The 2-alkylidene-3-alkenals can be used for altering the organoleptic properties of consumable materials as further described herein. It will thus be appreciated from the present disclosure that in certain embodiments the alkenal is formed from the alkynal by selective reduction of the triple bond to a double bond.

The alkyl groups contemplated herein are desirably lower alkyl groups containing from one to four carbon atoms. In view of the utility of the alkenals certain preferred embodiments contemplate that the alkyl groups represented by $R_1$ or $R_2$ are methyl or ethyl and those represented by $R_3$ or $R_4$ are methyl, ethyl, n-propyl, isopropyl, isobutyl and n-butyl.

It will be understood from the present disclosure that several cis-trans isomers are possible at the double bonds and are contemplated herein. As an instance, a particularly preferred alkenal is trans-2-ethylidene-cis-3-hexenal, the compound according to the foregoing formula when $R_1$ is methyl, $R_3$ is ethyl, and $R_2$ and $R_4$ are hydrogen. The structure of this compound can be written:

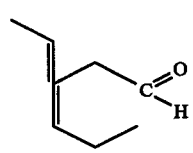

This configuration represents the one in which the methyl group represented by $R_1$ is trans to the carbonyl group and R₃ is cis with respect to the adjacent carbon-carbon double bond and in the "alkenal" chain.

The trans-2-ethylidene-cis-3-hexenal,

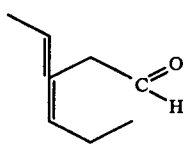

has a citrus, albedo-like character which ideally suits it for use in citrus flavors and particularly orange. In orange drink it imparts a juice-like character and improves the sweetness. 2-Ethylidene-6-methyl-cis-3-heptenal,

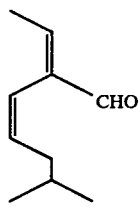

has a green, floral, slightly cucumber top fragrance note with a twig-like undertone particularly suiting it for use in fragrance compositions.

The 2-alkylidene-3-alkenal derivatives and mixtures thereof according to the present invention can be used to alter, vary, fortify, modify, enhance, or otherwise improve the organoleptic properties, including flavor and/or aroma, of a wide variety of materials which are ingested, consumed, or otherwise organoleptically sensed. The term "alter" in its various forms will be understood herein to mean the supplying or imparting a flavor character or note to an otherwise bland, relatively tasteless substance, or augmenting an existing flavor characteristic where the natural flavor is deficient in some regard, or supplementing the existing flavor or aroma impression to modify the organoleptic character. The materials which are so altered are generally referred to herein as consumable materials.

The starting material utilized in carrying out the present invention is a metallo actylide having the formula:

wherein the R is an alkyl group, desirably a lower alkyl group, and M represents a metal or a metallic compound. The metallic constituent can be an alkali metal such as lithium, sodium or potassium, or it can be a metallo compound such as a magnesium halide (Grignard reagent). A preferred alkali metal for use herein is lithium. Such metallo acetylides can be obtained by reacting alkyl acetylene having the formula:

with an appropriate organometallic reagent or an appropriate base.

Thus, the alkylacetylene compound is reacted with an organometallic alkyl or aryl alkali metal compound or an alkyl magnesium halide. Metallic bases such as alkali metal amides (e.g. NaNH₂) or N-alkyl-substituted amides can also be used. Examples of desirable materials used to form the metallo acetylide include butyl lithium, lithium amide, sodium amide, an alkyl magnesium bromide (e.g. CH₃MgBr), an alkyl magnesium chloride (e.g. CH₃MgCl) and the like.

The reaction to form the metallo acetylide is desirably carried out with a substantially stoichiometric quantity of the metallic compound, and it is preferable that the metallic compound not be in excess. This step is preferably carried out in the presence of a vehicle to moderate and control the reaction. Suitable vehicles include solvents such as dialkyl ethers or aromatic hydrocarbons. A preferred ether is diethyl ether and preferred hydrocarbons include benzene, toluene, and the like. When Grignard reagents are formed by the reaction of magnesium with a halide, this step of the reaction is preferably carried out in an oxygenated vehicle such as diethyl ether.

Except where otherwise stated, the steps described herein can be carried out above or below atmospheric pressure, and it is generally preferred to carry out such steps at substantially atmospheric pressure.

The metallo acetylide is reacted with a dialkoxy acetonitrile. The alkoxy groups can be those containing from one to six carbon atoms and the alkoxy groups containing about one or two carbon atoms are preferred. The acetylide and nitrile can be admixed in any order in the same vehicle and at the same temperatures used to form the metallo acetylide.

The reaction product formed by the reaction of the nitrile with the metallo acetylide, an imine salt, is then hydrolyzed (preferably without isolating it) in an aqueous acidic medium to provide a 1,1-dialkoxy-3-alkyne-2-one. The hydrolysis of the imine is carried out with dilute mineral acid such as sulfuric acid, hydrochloric acid and the like, or with an aqueous organic acid, desirably a lower carboxylic acid having from two to four carbon atoms, such as acetic acid and the like.

The hydrolysis can be carried out at temperatures of from about 0° to room temperature (approximately 30° C). The concentration of organic acid in the aqueous mixture is desirably 3 molar or less, and the concentration of the alternate aqueous mineral acid is desirably one molar or less.

The reaction of the metallo acetylide and nitrile and subsequent hydrolysis of the imine products causes production of an acetylenic ketone having the formula:

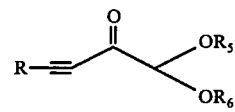

wherein R is as set forth above and R₅ and R₆ are the same or different lower alkyl groups of the dialkoxy acetonitrile e.g. methyl, ethyl, n-propyl, isopropyl, isobutyl and n-butyl.

This ketone may then be reacted with an alkylidene tri-substituted phosphorane having the formula (R₇)₃P=CH—R' wherein R' is the alkyl group represented by R₁ or R₂ and R₇ is aryl. Such phosphoranes can be prepared by admixing an alkyl tri-substituted phosphonium halide with a base to provide the alkylidene tri-substituted phosphorane. The phosphonium halide is the chloride, iodide, the bromide, and the three substituents in addition to the alkylidene group are aryl, preferably phenyl. Accordingly, R₇ is preferably phenyl.

The phosphorane, $(R_7)_3P=CH-R'$, is readily prepared in preferred embodiments by reacting the suitable alkyl-substituted triaryl phosphonium halide with a base such as an alkyl or aryl lithium; preferably phenyllithium or ethyllithium, or an alkali metal amide, preferably sodium amide.

The reaction to form the phosphorane is carried out at temperatures of from about 0° to about 40° C. The reaction is desirably carried out in an inert reaction vehicle compatible with the base, preferably one which is also a solvent for the alkynone, such as benzene, toluene, xylene, diethyl ether, and in the case of sodamide, liquid ammonia. The quantities of base and phosphonium halide utilized are desirably approximately stoichiometric, although a slight excess up to about 5 percent on a molar basis can be tolerated. The alkynone is slowly added to the phosphorane while the temperature is maintained at from about 0° to about 50° C. The reaction of dialkoxy alkynone and the phosphorane provides the 1,1-dialkoxy-2-alkylidene-3-alkyne having the formula:

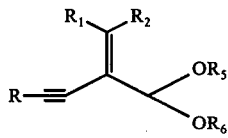

wherein one of $R_1$ and $R_2$ is the alkyl group represented by R' in the phosphorous compound and the other is hydrogen and R, $R_5$ and $R_6$ are lower alkyl as stated above.

The alkylidenation reaction also may be carried out using alkylidene phosphorous triamides having the formula:

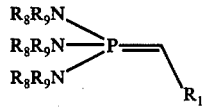

(See Ann. 682, 58 (1965) or alkyl phosphoramide anionic compounds having the structure:

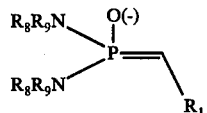

(See J. Am. Chem. Soc. 88, 5652 and 5653 (1966) wherein $R_1$ is defined above and $R_8$ and $R_9$ taken separately are each the same or different lower alkyl (e.g. methyl, ethyl and isopropyl) or taken together represent lower alkylidene (e.g. 1,2-ethylidene, 1,2-propylidene and 1,3-propylidene).

The alkylidenation reaction may, alternatively, be carried out using an appropriate Grignard reagent reaction sequence in three steps as follows:

(i) Reaction of the 1,1-dialkoxy-3-alkyne-2-one in a suitable solvent (e.g. diethyl ether) with ethyl, or propyl magnesium halide (e.g. iodide, chloride or bromide) R"MgX (R" being $R_1$ or $R_2$ and X being chloro, bromo or iodo) to form an organometallic compound having the structure:

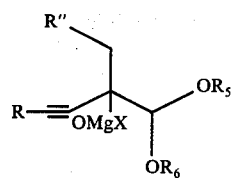

wherein R, $R_5$ and $R_6$ are as defined above;

(ii) Hydrolyzing the organometallic compound in aqueous dilute protonic acid (e.g. HCl or $H_2SO_4$) to form the corresponding hydroxy compound having the structure:

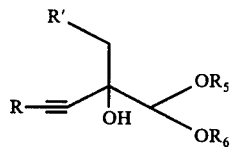

and (iii) dehydrating the said hydroxy compound to form the 1,1-dialkoxy-2-alkylidene-3-alkyne by means of heating with a mixture of acetic and oxalic acids at reflux conditions.

The alkoxy alkylidene alkyne may then be hydrolyzed to provide the novel alkynals having the formula:

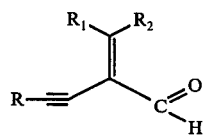

wherein R, $R_1$ and $R_2$ have the meaning stated above.

Alternatively, the alkoxy alkylidene alkyne can be first hydrogenated to provide the olefinic analog:

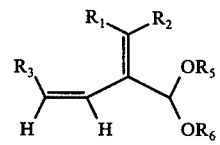

which analog can be hydrolyzed to obtain the corresponding 2-alkylidene-3-alkenal:

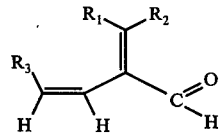

wherein $R_1$ and $R_2$ are as stated above and $R_3$ is the alkyl group represented by R. It will also be understood from the present disclosure that the 2-alkylidene-3-alkenal can also be prepared by hydrogenation of the novel alkynals set forth above.

The hydrogenation of the triple bond to a double bond and the hydrolysis of the dialkoxy derivatives (acetals) to the corresponding aldehyde are carried out in similar fashion regardless of the sequence of operations. Accordingly, it will be understood from the present description that the hydrogenation and acetal hydrolysis can be carried out in any order, and the description applies to either sequence.

Hydrogenation is carried out under conditions so that the triple (acetylenic) bond in the acetal or aldehyde is reduced to a double (olefinic) bond. The hydrogenation is catalytic; the catalysts are metallic hydrogenation catalysts, the activity of which has been reduced by a suitable deactivation (or poisoning) technique.

One such catalyst is palladium on a conventional support such as carbon, barium sulfate, calcium carbonate, and the like. The palladium is deactivated by treating it with a lead compound, desirably the lead salt of a lower aliphatic carboxylic acid having from two to four carbon atoms, such as lead acetate and the like. Metallic catalysts such as Raney nickel can also be used, provided the catalyst is deactivated, as by ageing or by addition of a deactivating material such as copper and the like.

The hydrogenation is desirably carried out in an inert reaction vehicle to moderate and control the hydrogenation. The reaction vehicle can be hydrocarbon such as an aliphatic or aromatic material like hexane, heptane, benzene, toluene, xylene, and the like, or it can be pyridine. Quinoline can also be added as a catalyst poison. It is generally preferred that the concentration of acetylenic material to be hydrogenated is 20 percent or less of the mixture. All parts, percentages, proportions, and ratios herein are by weight unless otherwise indicated.

The hydrogenation is desirably carried out at a temperature of from about 0° to about 80° C. The pressure utilized is desirably from about one to about five atmospheres. The amount of catalyst used, together with the temperature and pressure, determine the rate of the reaction and catalyst amounts of from one to about ten percent of the acetylenic substance are preferred.

Alternatively, the hydrogenation step may be performed under substantially the aforementioned conditions directly on the 1,1-dialkoxy-3-alkyne-2-one forming a 1,1-dialkoxy-3-alken-2-one which may then be alkylidenated in the same ways that the alkylidenation is performed on the 1,1-dialkoxy-3-alkyn-2-one.

It is significant that hydrogenation of the 1,1-dialkoxy-3-alkyne-2-one will yield, primarily, the isomer 1,1-dialkoxy-cis-3-alkene-2-one which may be isomerized, if desired, to the 1,1-dialkoxy-trans-3-alkene-2-one, using an appropriate cis-trans isomerization reagent such as a mixture of acetic acid and sodium iodide or potassium iodide (Preferred concentration range of alkali metal iodide in acetic acid, from 0.5% up to 2% by weight).

The hydrolysis of the acetal to the corresponding aldehyde is carried out in generally the same manner as set forth above for hydrolysis of the imine to the ketone using higher acid concentrations.

It should be noted that hydrolysis of the 1,1-dialkoxy-2-alkylidene-3-alkene produced as a result of reaction of the tri-substituted alkylidene phosphorane with the 1,1-dialkoxy-3-trans-alkene-2-one will yield a mixture of cis-2-alkylidene-trans-3-alkenal and trans-2-alkylidene-trans-3-alkenal. The cis-2-alkylidene-trans-3-alkenal in the mixture may then be specifically isomerized to the trans-2-alkylidene-trans-3-alkenal (thus creating a material containing only the one isomer, to wit: trans-2-alkylidene-trans-3-alkenal) by means of an appropriate cis-trans isomerization agent such as a mixture of acetic acid and an alkali metal iodide such as sodium iodide or potassium iodide (Preferred concentration range of alkali metal iodide in acetic acid from 0.5% up to 2% by weight).

The intermediate and/or final products obtained can be purified or isolated by conventional purification after appropriate washing, neutralizing and/or drying as appropriate. Thus, such products can be purified and/or isolated by distillation, steam distillation, vacuum distillation, extraction, preparative chromatographic techniques, and the like.

The following examples are given to illustrate embodiments of the invention as it is presently preferred to practice it. It will be understood that these examples are illustrative, and the invention is not to be considered as restricted thereto except as indicated in the appended claims.

EXAMPLE I

PREPARATION OF 2-ETHYLIDENE-CIS-3-HEXENAL (i) Preparation of 1,1-Dimethoxy-3-hexyne-2-one An ether solution of ethylmagnesium bromide is prepared from 7.3 g magnesium turnings and 32.7 g ethyl bromide. About 20 g of ethyl acetylene is admitted as a gas under a dry ice condenser and the mixture is refluxed for two hours until gas evolution ceases. The mixture is then cooled below 0°, and 30.3 g of dimethoxyacetonitrile is added in ether solution.

The mixture is allowed to come to room temperature and stirred for two hours, during which time the lower layer of the two-phase mixture becomes almost solid. The mixture is again cooled and treated with 16 ml sulfuric acid diluted with 300 ml water. The layers are separated and the organic layer is washed successively with saturated aqueous sodium chloride solution and saturated aqueous sodium bicarbonate solution and then dried over 4A molecular sieves. Thorough removal of solvent gives 35.3 g of yellow oil — 99% pure by GLC (gas-liquid phase chromatography).

(ii) Preparation of 2-Ethylidene-3-hexynal Dimethyl Acetal

Ethyltriphenylphosphonium bromide (24.8 g) is stirred with 100 ml benzene, and 40 ml (1.6 N) butyl lithium in hexane is added over about one-half hour with a water bath used to take up the slight heat of reaction. The mixture (bright orange) is stirred at room temperature for 0.75 hour, and 10.0 g of the 1,1-dimethoxy-3-hexyne-2-one is added dropwise in one-half hour.

After an additional 15 minutes at 40° C (water bath) the mixture is filtered and evaporated at reduced pressure through a fractionation column. The residue is dissolved in isopentane, filtered, and again evaporated to provide 4.3 g of a yellow orange oil. Gas chromatographic, mass spectral and nuclear magnetic resource (NMR) data indicate that the major peaks are isomers of the desired structures:

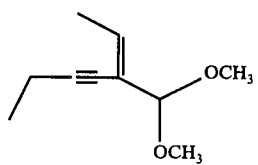

-continued

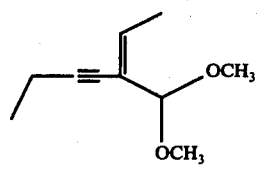

(iii) Preparation of 2-Ethylidene-3-hexynal

The acetal isomers so produced are dissolved in 50 ml ether and stirred for 1½ hours with 25 ml water containing 2.5 g oxalic acid (room temperature). The organic layer is separated and washed successively with saturated aqueous sodium carbonate solution and brine, and evaporated at atmospheric pressure through a Vigreux column. After removal of the last traces of solvent in vacuo there remains 3.0 g of reddish oil. GC-MS and NMR confirm that the major product is 2-ethylidene-3-hexynal.

(iv) Preparation of 2-Ethylidene-cis-3-hexenal

The 2-ethylidene-3-hexynal so prepared (2.5 g) is dissolved in 20 ml hexane and a small amount of solid is removed by filtration through a pad of neutral alumina. The solution is then mixed with 0.25 g Lindlar catalyst (palladium on calcium carbonate poisoned with lead acetate) and stirred under hydrogen gas at about one atmosphere pressure for 6½ hours. The resulting mixture is filtered and the solvent removed through a Vigreux column. The major component, isolated from a Carbowax (polyethylene glycol)-packed GLC column is demonstrated by IR (infrared) NMR- and MS spectral data to be

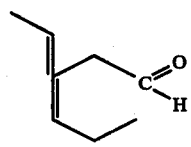

The other 2-alkylidene-3-alkenals are similarly prepared.

In the following NMR spectra, the shifts in ppm relative to a tetramethylsilane standard are measured in carbon tetrachloride at 100 MHz. The 2-ethylidene-cis-3-hexenal produced in Example I shows the following:

| Shift | No. of Protons | Peak | Assignment |
|---|---|---|---|
| 0.92 | 3 | Triplet | $CH_3$—$CH_2$— |
| 1.88 | 5 | Doublet | $CH_3$—C=C—C=O |
| 1.92-1.70 | | Multiplet | $CH_3$—$CH_2$—C=C— |
| 5.75 | 2 | Multiplet | Olefinic protons |
| 6.61 | 1 | Quartet | $CH_3$—CH=C—C=O |
| 9.41 | 1 | Singlet | Formyl proton |

EXAMPLE II

Preparation of 2-Ethylidene-6-methyl-cis-3-heptenal

A solution of 5.40 g of isobutylacetylene in 50 ml of diethyl ether is treated with 30 ml of 2.2 N n-butyllithium in hexane at −20° C, and after several minutes the resulting solution is treated with 8.50 g of diethoxyacetonitrile and then warmed slowly to room temperature. After about 1.5 hours the dark mixture is cooled and brought to a pH of about 2 with ten percent sulfuric acid.

The layers are then separated and the organic layer is washed successively with water and saturated aqueous sodium bicarbonate solution and then dried over sodium sulfate. Evaporation of the solvent provides 4.6 g of a dark oil, shown by IR and NMR to contain 1,1-diethoxy-6-methyl-3-heptyn-2-one.

A solution of ethylidenetriphenylphosphorane is prepared by admixing 17.0 g of ethyltriphenylphosphonium bromide with 20 ml of 2.3 N phenyllithium in a 70:30 benzene: ether vehicle. This is added to the resulting octynone with the temperature being held below 30° C with cooling.

A few minutes after the addition is completed, the mixture is partitioned between water and ether phases. The layers are separated, and the organic phase is dried over sodium sulfate and evaporated. The residue is dissolved in hexane and filtered to remove triphenylphosphine oxide. After evaporation of the hexane, the 10.4 g of crude acetal obtained is hydrolyzed to the acetylenic aldehyde in 30 percent aqueous acetic acid.

The crude aldehyde is isolated by partitioning between water and ethyl; the ether layer is washed successively with water and saturated aqueous sodium carbonate and dried over sodium sulfate; and the solvent is evaporated. The residue is hydrogenated in hexane solution over 1.0 g of Lindlar catalyst (5 percent palladium on calcium carbonate poisoned with lead acetate) at a pressure of about four atmospheres.

The mixture is filtered and the solvent is evaporated to provide 3.8 g of dark oil from which the 2-ethylidene-6-methyl-cis-3-heptenal is isolated by preparative GLC. The NMR spectrum of the material shows:

| Shift | No. of Protons | Peak | Assignment |
|---|---|---|---|
| 1.00 | 6 | Doublet | —HC($CH_3$)$_2$ |
| 1.70 | 2 | Quartet | =C—$CH_2$ |
| 1.88 | 3 | Doublet | —CO—C=C—$CH_3$ |
| 5.80 | 2 | Multiplet | Olefinic protons |
| 6.70 | 1 | Quartet | $CH_3$—CH=C—C=O |
| 9.37 | 1 | Singlet | Formyl proton |

The material

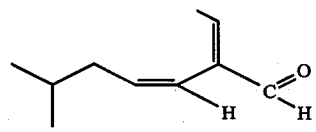

has a green, floral, violet, slightly cucumber fragrance.

EXAMPLE III

Preparation of 1,1-Dimethoxy-cis-3-hexene-2-one

Six grams of the 1,1-dimethoxy-3-hexyne-2-one (of Example I) is stirred under hydrogen gas at one atmosphere in 40 ml hexane containing 0.6 g Lindlar catalyst (palladium on calcium carbonate poisoned with lead acetate) and 4.0 g quinoline. The reaction is terminated when one percent of the starting material (1,1-dimethoxy-3-hexyne-2-one) remains after about 1½ hours.

The mixture is filtered and the quinoline washed out with dilute aqueous hydrochloric acid. The organic layer is washed with saturated aqueous sodium bicarbonate and then brine; and the solvent is evaporated. GLC and NMR of the crude material show the product is substantially 1,1-dimethoxy-cis-3-hexene-2-one having the structure:

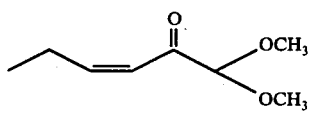

EXAMPLE IV

Preparation of 1,1-Dimethoxy-trans-3-hexene-2-one

The crude product produced in Example III is dissolved in 6 ml of acetic acid with 0.1 g of sodium iodide. By GLC analysis on Carbowax (polyethylene glycol) it is clear that the 1,1-dimethoxy-cis-3-hexene-2-one is converted to a new material of later retention time. After one-half hour less than 5 percent of "cis" material remains.

The material is isolated by partitioning between water and ether, washing the ether layer successively with aqueous sodium bicarbonate and brine and then drying over 4A molecular sieves. Evaporation of the solvent provides 5.0 g of yellow oil. NMR and GLC indicate essentially all "trans" material having the structure:

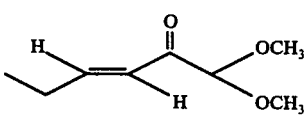

EXAMPLE V

Preparation of trans-2-Ethylidene-trans-3-hexenal

Ethyltriphenylphosphonium bromide (3.71 g) and 6.3 ml of 1.6 N n-butyl lithium are mixed in ether solution and 1.58 g of the 1,1-dimethoxy-trans-3-hexene-2-one of Example IV is added, while keeping the internal temperature below 30° C. After a few minutes the mixture is filtered and the solvent evaporated. A small amount of solid is present so the residue is dissolved in isopentane, filtered, and again evaporated to give 1.10 g of a yellow-orange oil.

GLC and NMR indicate the presence of two acetals of 2-ethylidene-trans-3-hexenal: cis and trans isomers at the ethylidene group, namely: cis-2-ethylidene-trans-3-hexenal dimethyl acetal and trans-2-ethylidene-trans-3-hexenal dimethyl acetal. The acetal material is dissolved in 2 ml water and 3 ml acetic acid with a small amount of sodium iodide. After a few minutes GLC obtained on a 10 foot by one-eighth inch DC-710 (20%) shows complete hydrolysis. (In the absence of sodium iodide a mixture of cis and trans ethylidene isomers of 2-ethylidene-trans-3-hexenal is obtained).

The product is isolated by partitioning between water and ether. The organic layer is washed successively in water, aqueous sodium bicarbonate, and aqueous sodium chloride and finally evaporated to give 0.70 g of an orange oil. The major peak (80%), isolated by preparative GLC is trans-2-ethylidene-trans-3-hexenal having the structure:

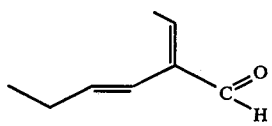

EXAMPLE VI

Preparation of (Z)-2-Ethylidene-(Z)-3-hexenal (or cis-2-ethylidene-cis-3-hexenal)

A slurry of 4.20 g ethyltriphenylphosphonium iodide in 30 ml ether is mixed with 4.3 ml 2.3 N phenyllithium in benzene: ether to provide a deep orange solution. 1,1-Dimethoxy-3-hexyne-2-one as obtained in Example I (1.56 g) is added, keeping the temperature below 30°, and the resulting mixture is stirred 1 hour. Water and more ether are added, the mixture is filtered, the layers separated, and the organic layer washed with brine and then evaporated.

The residue is dissolved in isopentane, filtered, and evaporated to give 2.0 g of orange-colored oil. The crude product is hydrogenated at about one atmosphere pressure in 10 ml pyridine over 0.2 g palladium on barium sulfate and the material is re-isolated by partitioning between ether and water. The organic layer is washed several times with water and then saturated aqueous sodium chloride.

After removal of solvent there is a red-orange oil which contains some pyridine. The major product is isolated by preparative GLC. The trapped material (140 mg.) is hydrolyzed by stirring it in ether solution with 5 percent sulfuric acid. After 1½ hours at room temperature the mixture is worked up by separating the layers, washing the ether layer with aqueous sodium bicarbonate followed by saturated aqueous sodium chloride and evaporating through a Vigreux column to give 110 mg of a very pale green oil with a fresh "green" aroma.

By GLC it is found to contain 10 percent of the acetal, and by NMR, to contain 20 percent of the stable isomer. The major product is the 2-cis-ethylidene-3-cis-hexenal isomer with the structure:

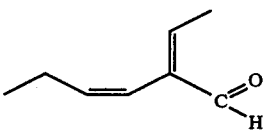

EXAMPLE VII

Orange Flavor Formulation

An orange flavor formulation is prepared by admixing:

| Ingredients | Parts |
| --- | --- |
| Natural orange oil | 13.00 |
| Acetaldehyde | 1.50 |
| Ethyl acetate | 0.10 |
| Ethyl butyrate | 0.50 |
| Propanol | 0.10 |
| trans-2-Hexenal | 0.10 |
| Ethyl Alcohol (95%) | 60.00 |
| Fusel Oil | 0.05 |
| Propylene Glycol | 24.65 |

This is denominated Flavor "A". A second formulation, Flavor "B", is prepared by adding 2-ethylidene-cis-3-hexenal (one percent in ethanol [Produced according to Example I]) to a portion of Flavor "A" in the ratio of 2 parts to 100 parts of Flavor "A".

Each of Flavors "A" and "B" is added in the amount of 2 ounces per gallon of 32° Baume sugar syrup to produce a syrup for combination with water to form a drink. The beverage prepared using Flavor "A" is a passable orange beverage of good character, flavor and intensity.

The beverage prepared using Flavor "B" has a much improved flavor. The improvement contributed by the ethylidenehexenal is due to:

1. a greater degree of the natural character of freshly squeezed orange juice.
2. an increase in the pulplike notes
3. greater orange juice flavor depth.

EXAMPLE VIII (Preparation of Trans-2-Ethylidene-Cis-3-Hexenal From 1,1-Dimethoxy-Cis-3-Hexane-2-One)

An ether suspension of 19.0 g ethyl-triphenylphosphonium bromide is treated with 22 ml of 2.3 N phenyllithium in 70:30 benzene-ether, keeping the reaction temperature below 30° C. The resulting orange-red solution is stirred in an ice bath while 7.40 g of 1,1-dimethoxy-cis-3-hexene-2-one (produced by the process of Example III) is added dropwise. After the addition, the mixture is allowed to warm to room temperature and then stirred with 20 ml 1N HCl for 0.5 hours. The layers are separated and the solvent is removed from the organic layer. The residue is taken up in pentane and filtered to remove triphenylphosphonium oxide. Removal of the solvent then gives 5.20 g of an orange-colored oil. The major component isolated by GLC (carbowax column), is trans-2-ethylidene-cis-3-hexenal whose spectral characteristics are the same as reported in Example I.

What is claimed is:

1. A process for the production of a trans-2-alkylidene-trans-3-alkenal which comprises the steps of:

(i) Hydrogenating a first oxo compound having the formula:

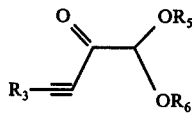

to provide a second oxo compound having the structure:

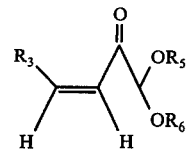

in the presence of a deactivated metallic hydrogenation catalyst selected from the group consisting of deactivated Palladium and deactivated Raney Nickel, said hydrogenation being carried out in an inert reaction vehicle, the concentration of said first oxo compound in said reaction vehicle being 20% by weight or less of said reaction mass, said hydrogenation being carried out at a temperature of from about 0° C up to about 80° C and at a pressure of from about 1 up to about 5 atmospheres, the quantity of catalyst being from 1 up to about 10% by weight of said first oxo compound;

(ii) Reacting said second oxo compound with a phosphorous compound having the formula:

to form a mixture of cis and trans 2-alkylidene-cis-3-alkenal acetals represented by the structure:

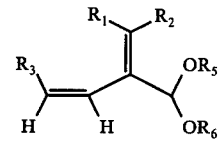

said reaction between said second oxo compound and said phosphorous compound being carried out at a temperature of from about 0° C up to about 50° C; wherein $R_5$ and $R_6$ are the same or different lower alkyl; in one of the compounds of the resulting mixture, $R_1$ is lower alkyl and $R_2$ is hydrogen; in the other of the compounds of the resulting mixture $R_2$ is lower alkyl and $R_1$ is hydrogen; $R'$ is a lower alkyl equivalent to $R_1$ or $R_2$; and $R_7$ is phenyl;

(iii) Hydrolyzing said mixture of cis and trans 2-alkylidene cis-3-alkenal acetal to form a mixture of cis and trans-2-alkylidene-cis-3-alkenals, with dilute mineral acid or with an aqueous organic acid at a temperature of from about 0° C up to about 30° C, the concentration of said acid being in an amount sufficient to hydrolyze said mixture of cis and trans-2-alkylidene-cis-3-alkenal acetals to said mixture of said cis and trans-2-alkylidene-cis-3-alkenals; and (iv) Isomerizing the cis-2-alkylidene-trans-3-alkenal in the said mixture of cis and trans-2-alkylidene-cis-3-alkenals to trans-2-alkylidene-trans-3-alkenal thereby creating one isomer, trans-2-alkylidene-trans-3-alkenal, by contacting said mixture of cis and trans-2-alkylidene-cis-3-alkenals with an isomerizing agent, which isomerizing agent is a mixture of acetic acid and an alkali metal iodide, the concentration range of alkali metal iodide in acetic acid being from 0.5% up to 2% by weight, the isomerization taking place at a temperature of from about 0° C up to about 30° C.

* * * * *